(12) United States Patent
Jacobsen et al.

(10) Patent No.: US 7,787,939 B2
(45) Date of Patent: Aug. 31, 2010

(54) MINIATURIZED IMAGING DEVICE INCLUDING UTILITY APERTURE AND SSID

(75) Inventors: Stephen C. Jacobsen, Salt Lake City, UT (US); David T. Markus, Salt Lake City, UT (US); Ralph W. Pensel, Sandy, UT (US)

(73) Assignee: Sterling LC, Salt Lake City, UT (US)

( * ) Notice: Subject to any disclaimer, the term of this patent is extended or adjusted under 35 U.S.C. 154(b) by 1339 days.

(21) Appl. No.: 10/391,490

(22) Filed: Mar. 17, 2003

(65) Prior Publication Data
US 2003/0220574 A1 Nov. 27, 2003

Related U.S. Application Data

(60) Provisional application No. 60/365,561, filed on Mar. 18, 2002, provisional application No. 60/365,692, filed on Mar. 18, 2002, provisional application No. 60/431,261, filed on Dec. 6, 2002.

(51) Int. Cl.
*A61B 6/00* (2006.01)
(52) U.S. Cl. .................. 600/476; 600/109; 348/65; 348/76
(58) Field of Classification Search ............... 600/109, 600/110, 129, 130, 476; 348/65–76
See application file for complete search history.

(56) References Cited

U.S. PATENT DOCUMENTS

| | | | |
|---|---|---|---|
| 3,817,635 A | 6/1974 | Kawahara | |
| 3,856,000 A | 12/1974 | Chikama | |
| 3,971,065 A | 7/1976 | Bayer | |
| 4,283,115 A | 8/1981 | Fraissl | |
| 4,487,206 A | 12/1984 | Aagard | |

(Continued)

FOREIGN PATENT DOCUMENTS

CN 1481753 3/2004

(Continued)

OTHER PUBLICATIONS

Jacobsen, Stephen C., U.S. Appl. No. 10/391,489, filed Mar. 17, 2003.

(Continued)

*Primary Examiner*—Brian Casler
*Assistant Examiner*—Peter Luong
(74) *Attorney, Agent, or Firm*—Thorpe North & Western LLP (57) ABSTRACT

The present invention is drawn toward miniaturized imaging devices. In one embodiment, the device can include a utility guide having at least one aperture configured for supporting utilities, and an SSID carried by the utility guide. The SSID can include an imaging array on a top surface, and a conductive element on a side surface, wherein the imaging array is electrically coupled to the conductive element. Further, a lens can be optically coupled to the imaging array, and an umbilical, including a conductive line, can be carried by the at least one aperture. The conductive line can be electrically coupled to the conductive element on the side surface of the SSID. Alternatively, the device can include an SSID having, as an integral structure, an imaging array electrically coupled to a conductive pad, wherein the SSID further includes at least one utility aperture passing therethrough. Further, a lens can be optically coupled to the imaging array, and an umbilical, including a conductive line carried by the at least one aperture, can be configured such that the conductive line is directly electrically coupled to the conductive pad.

17 Claims, 10 Drawing Sheets

U.S. PATENT DOCUMENTS

| | | | |
|---|---|---|---|
| 4,491,865 A | 1/1985 | Danna et al. | |
| 4,515,444 A | 5/1985 | Prescott et al. | |
| 4,573,450 A | 3/1986 | Arakawa | |
| 4,594,613 A | 6/1986 | Shinbori et al. | |
| 4,604,992 A | 8/1986 | Sato | |
| 4,620,534 A | 11/1986 | Zartman | |
| 4,622,954 A | 11/1986 | Arakawa et al. | |
| 4,646,724 A | 3/1987 | Sato et al. | |
| 4,706,118 A | 11/1987 | Kato et al. | |
| 4,723,843 A | 2/1988 | Zobel | |
| 4,745,470 A | 5/1988 | Yabe et al. | |
| 4,745,471 A | 5/1988 | Takamura et al. | |
| 4,791,479 A | 12/1988 | Ogiu et al. | |
| 4,802,487 A | 2/1989 | Martin et al. | |
| 4,803,562 A | 2/1989 | Eino | |
| 4,832,003 A | 5/1989 | Yabe | |
| 4,846,785 A | 7/1989 | Cassou et al. | |
| 4,859,040 A | 8/1989 | Kitagishi et al. | |
| 4,867,137 A | 9/1989 | Takahashi | |
| 4,867,138 A | 9/1989 | Kubota et al. | |
| 4,867,174 A | 9/1989 | Skribiski | |
| 4,880,298 A | 11/1989 | Takada | |
| 4,895,138 A | 1/1990 | Yabe | |
| 4,926,257 A | 5/1990 | Miyazaki | |
| 4,932,394 A | 6/1990 | Nanaumi | |
| 4,998,807 A | 3/1991 | Uzawa et al. | |
| 5,006,928 A | 4/1991 | Kawajiri et al. | |
| 5,009,483 A | 4/1991 | Rockwell, III | |
| 5,021,888 A | 6/1991 | Kondou et al. | |
| 5,040,069 A | 8/1991 | Matsumoto et al. | |
| 5,061,036 A | 10/1991 | Gordon | |
| 5,093,719 A | 3/1992 | Prescott | |
| 5,106,387 A | 4/1992 | Kittrell et al. | |
| 5,109,859 A | 5/1992 | Jenkins | |
| 5,111,804 A | 5/1992 | Funakoshi | |
| 5,113,254 A | 5/1992 | Kanno et al. | |
| 5,130,804 A | 7/1992 | Tamura et al. | |
| 5,166,656 A | 11/1992 | Badihi et al. | |
| 5,191,203 A | 3/1993 | McKinley | |
| 5,198,894 A | 3/1993 | Hicks | |
| 5,220,198 A | 6/1993 | Tsuji | |
| 5,222,477 A | 6/1993 | Lia | |
| 5,228,430 A | 7/1993 | Sakamoto | |
| 5,258,834 A | 11/1993 | Tsuji et al. | |
| 5,289,434 A | 2/1994 | Berni | |
| 5,291,010 A | 3/1994 | Tsuji | |
| 5,304,173 A | 4/1994 | Kittrell et al. | |
| 5,305,098 A | 4/1994 | Matsunaka et al. | |
| 5,318,024 A | 6/1994 | Kittrell et al. | |
| 5,361,166 A | 11/1994 | Atkinson et al. | |
| 5,365,268 A | 11/1994 | Minami | |
| 5,376,960 A | 12/1994 | Wurster | |
| 5,377,047 A | 12/1994 | Broome et al. | |
| 5,381,784 A | 1/1995 | Adair | |
| 5,396,366 A | 3/1995 | Brown et al. | |
| 5,398,685 A | 3/1995 | Wilk et al. | |
| 5,402,769 A | 4/1995 | Tsuji | |
| 5,430,475 A | 7/1995 | Goto et al. | |
| 5,434,615 A | 7/1995 | Matumoto | |
| 5,436,655 A | 7/1995 | Hiyama et al. | |
| 5,438,975 A | 8/1995 | Miyagi et al. | |
| 5,455,455 A | 10/1995 | Badehi | |
| 5,458,612 A | 10/1995 | Chin | |
| 5,459,570 A | 10/1995 | Swanson et al. | |
| 5,469,841 A | 11/1995 | Kobayashi et al. | |
| 5,494,483 A | 2/1996 | Adair | |
| 5,512,940 A | 4/1996 | Takasugi et al. | |
| 5,531,664 A | 7/1996 | Adachi et al. | |
| 5,547,455 A | 8/1996 | McKenna | |
| 5,547,906 A | 8/1996 | Badehi | |
| 5,594,497 A | 1/1997 | Ahern et al. | |
| 5,603,687 A * | 2/1997 | Hori et al. | 600/166 |
| 5,630,788 A * | 5/1997 | Forkner et al. | 600/182 |
| 5,647,368 A | 7/1997 | Zeng et al. | |
| 5,673,083 A | 9/1997 | Izumi et al. | |
| 5,685,311 A * | 11/1997 | Hara | 600/459 |
| 5,693,043 A | 12/1997 | Kittrell et al. | |
| 5,704,892 A | 1/1998 | Adair | |
| 5,716,323 A | 2/1998 | Lee | |
| 5,716,759 A | 2/1998 | Badehi | |
| 5,722,403 A | 3/1998 | McGee et al. | |
| 5,740,808 A | 4/1998 | Panescu et al. | |
| 5,749,827 A | 5/1998 | Minami | |
| 5,751,340 A | 5/1998 | Strobl et al. | |
| 5,752,518 A | 5/1998 | McGee et al. | |
| 5,769,792 A | 6/1998 | Palcic et al. | |
| 5,772,597 A | 6/1998 | Goldberger et al. | |
| 5,776,049 A | 7/1998 | Takahashi | |
| 5,792,984 A | 8/1998 | Bloom | |
| 5,800,341 A | 9/1998 | McKenna et al. | |
| 5,808,665 A | 9/1998 | Green | |
| 5,818,644 A | 10/1998 | Noda | |
| 5,827,172 A | 10/1998 | Takahashi et al. | |
| 5,840,017 A | 11/1998 | Furusawa et al. | |
| 5,846,185 A | 12/1998 | Carollo | |
| 5,848,969 A | 12/1998 | Panescu et al. | |
| 5,865,729 A | 2/1999 | Meehan et al. | |
| 5,870,229 A | 2/1999 | Tsuchida | |
| 5,873,816 A * | 2/1999 | Kagawa et al. | 600/134 |
| 5,879,285 A | 3/1999 | Ishii | |
| 5,904,651 A | 5/1999 | Swanson et al. | |
| 5,908,445 A | 6/1999 | Whayne et al. | |
| 5,913,817 A | 6/1999 | Lee | |
| 5,916,155 A | 6/1999 | Levinson et al. | |
| 5,929,900 A | 7/1999 | Yamanaka et al. | |
| 5,940,126 A | 8/1999 | Kimura | |
| 5,947,894 A | 9/1999 | Chapman et al. | |
| 5,951,462 A | 9/1999 | Yamanaka | |
| 5,957,849 A | 9/1999 | Munro | |
| 5,971,915 A | 10/1999 | Yamamoto et al. | |
| 5,973,779 A | 10/1999 | Ansari et al. | |
| 5,980,663 A | 11/1999 | Badehi | |
| 5,999,327 A | 12/1999 | Nagaoka | |
| 6,008,123 A | 12/1999 | Kook et al. | |
| 6,022,758 A | 2/2000 | Badehi | |
| 6,040,235 A | 3/2000 | Badehi | |
| 6,095,970 A | 8/2000 | Hidaka et al. | |
| 6,117,707 A | 9/2000 | Badehi | |
| 6,118,476 A | 9/2000 | Morito et al. | |
| 6,133,637 A | 10/2000 | Hikita et al. | |
| 6,134,003 A | 10/2000 | Tearney et al. | |
| 6,139,489 A * | 10/2000 | Wampler et al. | 600/109 |
| 6,142,930 A | 11/2000 | Ito et al. | |
| 6,161,035 A | 12/2000 | Furusawa | |
| 6,184,923 B1 | 2/2001 | Miyazaki | |
| 6,211,955 B1 | 4/2001 | Basiji et al. | |
| 6,261,226 B1 | 7/2001 | McKenna et al. | |
| 6,319,745 B1 | 11/2001 | Bertin et al. | |
| 6,322,498 B1 | 11/2001 | Gravenstein et al. | |
| 6,327,096 B1 | 12/2001 | Tsuchida | |
| 6,352,503 B1 | 3/2002 | Matsue | |
| 6,366,726 B1 | 4/2002 | Wach et al. | |
| 6,384,397 B1 | 5/2002 | Takiar et al. | |
| 6,396,116 B1 | 5/2002 | Kelly et al. | |
| 6,485,413 B1 | 11/2002 | Boppart et al. | |
| 6,522,913 B2 | 2/2003 | Swanson et al. | |
| 6,533,722 B2 * | 3/2003 | Nakashima | 600/179 |
| 6,537,205 B1 | 3/2003 | Smith | |
| 6,561,972 B2 | 5/2003 | Ooshima et al. | |
| 6,595,913 B2 * | 7/2003 | Takahashi | 600/110 |
| 6,624,138 B1 | 9/2003 | Tu et al. | |
| 6,643,071 B2 | 11/2003 | Schnitzer | |
| 6,658,279 B2 | 12/2003 | Swanson et al. | |
| 6,695,787 B2 | 2/2004 | Hogendijk et al. | |

| | | | |
|---|---|---|---|
| 6,719,686 B2 | 4/2004 | Coakley et al. | |
| 6,761,684 B1 | 7/2004 | Speier | |
| 6,826,422 B1 | 11/2004 | Modell et al. | |
| 6,827,683 B2 | 12/2004 | Otawara | |
| 6,834,158 B1 | 12/2004 | Templeton | |
| 6,879,851 B2 | 4/2005 | McNamara et al. | |
| 6,898,458 B2 | 5/2005 | Zeng et al. | |
| 6,937,268 B2 | 8/2005 | Ogawa | |
| 6,953,432 B2 | 10/2005 | Schiefer | |
| 6,960,165 B2 | 11/2005 | Ueno et al. | |
| 6,982,740 B2 | 1/2006 | Adair et al. | |
| 7,030,904 B2 | 4/2006 | Adair et al. | |
| 7,033,317 B2 | 4/2006 | Pruitt | |
| 7,091,500 B2 | 8/2006 | Schnitzer | |
| 7,153,299 B1 | 12/2006 | Tu et al. | |
| 7,166,537 B2 | 1/2007 | Jacobsen et al. | |
| 7,218,822 B2 | 5/2007 | Treado et al. | |
| 7,221,388 B2 | 5/2007 | Sudo et al. | |
| 2001/0007051 A1 | 7/2001 | Nakashima | |
| 2001/0007511 A1 | 7/2001 | Minami et al. | |
| 2001/0024848 A1 | 9/2001 | Nakamura | |
| 2001/0049509 A1 | 12/2001 | Sekine et al. | |
| 2002/0007110 A1 | 1/2002 | Irion | |
| 2002/0080248 A1 | 6/2002 | Adair et al. | |
| 2002/0111534 A1 | 8/2002 | Suzuki et al. | |
| 2002/0166946 A1 | 11/2002 | Iizuka et al. | |
| 2002/0188204 A1 | 12/2002 | McNamara | |
| 2002/0193660 A1 | 12/2002 | Weber | |
| 2003/0071342 A1 | 4/2003 | Honda et al. | |
| 2003/0220574 A1 | 11/2003 | Markus et al. | |
| 2003/0222325 A1 | 12/2003 | Jacobsen | |
| 2004/0017961 A1 | 1/2004 | Petersen et al. | |
| 2004/0059204 A1 | 3/2004 | Marshall | |
| 2004/0181148 A1 | 9/2004 | Uchiyama et al. | |
| 2004/0225222 A1 | 11/2004 | Zeng et al. | |
| 2005/0054902 A1 | 3/2005 | Konno | |
| 2005/0154277 A1 | 7/2005 | Tang et al. | |
| 2005/0174649 A1 | 8/2005 | Okada et al. | |
| 2005/0234345 A1 | 10/2005 | Yang | |
| 2005/0267340 A1 | 12/2005 | Ishihara et al. | |
| 2005/0288555 A1 | 12/2005 | Binmoeller | |
| 2006/0069312 A1 | 3/2006 | O'Connor | |
| 2006/0146172 A1 | 7/2006 | Jacobsen et al. | |
| 2008/0045794 A1 | 2/2008 | Belson | |

FOREIGN PATENT DOCUMENTS

| | | |
|---|---|---|
| EP | 0482997 | 10/1991 |
| EP | 0639043 | 2/1995 |
| EP | 0681809 | 11/1995 |
| EP | 1104182 | 5/2001 |
| EP | 1477104 | 11/2004 |
| EP | 1626436 | 2/2006 |
| JP | 63-155115 | 6/1988 |
| JP | 5-049602 | 3/1993 |
| JP | 58-046924 | 3/1993 |
| JP | 08084700 | 4/1996 |
| JP | 2005334462 | 12/2005 |
| JP | 2007/312290 | 11/2007 |
| WO | WO99/40624 | 2/1998 |
| WO | WO98/38907 | 9/1998 |
| WO | WO00/54033 | 9/2000 |
| WO | WO 03/081831 | 10/2003 |
| WO | WO2006/060777 | 6/2006 |

OTHER PUBLICATIONS

Jacobsen, Stephen C., U.S. Appl. No. 10/391,513, filed Mar. 17, 2003.
Jacobsen, Stephen C., U.S. Appl. No. 11/810,702, filed Jun. 5, 2007.
Jacobsen, Stephen C., U.S. Appl. No. 12/079,741, filed Mar. 27, 2008.
Jacobsen, Stephen C., U.S. Appl. No. 12/008,486, filed Jan. 11, 2008.
Jacobsen, Stephen C., U.S. Appl. No. 11/292,902, filed Dec. 1, 2005.
Jacobsen, Stephen C., U.S. Appl. No. 12/487,495, filed Jun. 18, 2009.
Jacobsen, Stephen C., U.S. Appl. No. 12/487,481, filed Jun. 18, 2009.
Jacobsen, Stephen C., U.S. Appl. No. 12/512,188, filed Jul. 30, 2009.
Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.
J. Knittel et al., "Endoscope-compatible confocal microscope using a gradient index-lens system" Optics Communications, vol. 188, Issue 5-6, Feb 2001, pp. 267-273.
Nguyen, Clark T.-C., "Communications Applications of Microelectromechanical Systems," Proceedings of the 1998 Sensors Expo, San Jose, CA, May 19-21, 1998, 9 pages.
Fujimoto, JG et al., "High resolution in vivo intra-arterial imaging with optical coherence tomography," Heart, 1999, vol. 82, pp. 128-133.
Boppart, S.A. et al., "Forward-imaging instruments for optical coherence tomography," Optics Letters, Nov. 1, 1997, vol. 22, No. 21, pp. 1618-1620.
Tearney, G.J. et al., "Scanning single-mode fiber optic catheter-endoscope for optical coherence tomography," Optics Letters, Apr. 1, 1996, vol. 21, No. 7, pp. 543-545.
Boppart, S.A. et al., "Optical imaging technology in minimally invasive surgery," Surg. Endosc., 1999, vol. 13, pp. 718-722.
Zeis, Michael, et al., "Color Business Report", ISSN 1055-3339, Jul. 2002, p. 5.
Microcam, Minast Project 5.04, Nov. 11, 1999, http://www.imt.unine.ch/ESPLAB/www/projects/Microcam/, pp. 1-16.
Literature from Grin Tech, "In Vivo Medical Confocal Imaging and Optical Coherence Tomography", www.grintech.de, Revision Jun. 2001, pp. 1-3.

* cited by examiner

MINIATURIZED IMAGING DEVICE INCLUDING UTILITY APERTURE AND SSID

The present application claims priority to U.S. Provisional Application Nos. 60/365,561, 60/365,692, both filed Mar. 18, 2002 and 60/431,261, filed Dec. 6, 2002 each of which are incorporated herein by reference in their entirety.

FIELD OF THE INVENTION

The invention relates generally to solid state imaging devices (SSIDs). More specifically, the invention relates to miniaturized imaging devices that are particularly suited to viewing beyond small openings and traversing small-diameter areas. These devices can be used for catheter-borne medical imaging within the anatomy of a patient, and are useful for other applications.

BACKGROUND OF THE INVENTION

Small imaging devices that take advantage of advances in integrated circuit imaging technologies are known. Such small imaging devices can be particularly useful in medical diagnostic and treatment applications. Portions of human anatomy previously viewable only by a surgical procedure can be viewed now by a minimally invasive catheterization, provided an imaging device can be made that is small enough to view the target anatomy.

Other uses for very small imaging devices are recognized. For example, such devices can be used and are desirable for surveillance applications, for monitoring of conditions and functions within devices, and for size- and weight-critical imaging needs as are present in aerospace applications, to name a few.

While the present invention has applications in these aforementioned fields and others, the medical imaging application can be used to favorably illustrate unique advantages of the invention. The desirability of providing imaging at sites within the anatomy of living creatures, especially humans, distal of a small orifice or luminal space has long been recognized. A wide variety of types and sub-types of endoscopes have been developed for this purpose.

One advance in imaging technology which has been significant is in the area of SSIDs. Such devices, including the charge-injection device (CID), the charge-coupled device (CCD), and the complementary metal oxide semiconductor (CMOS) device, provide good alternatives to the use of bundled fiber optics, as well as to conventional miniaturized imaging devices used in endoscope applications. However, when considering a design of a catheter-borne imaging device, consideration should be given to the ability of a distal tip of the catheter to flex and bend, without breaking or becoming damaged. This is necessary to accommodate limitations of anatomy to minimize trauma, and to enable steering of the distal tip to a desired location.

Accordingly, there is a desire to manufacture smaller devices that are steerable and provide good image quality for the size.

SUMMARY OF THE INVENTION

It has been recognized that by looking outside conventional devices and techniques, that facilitation of further miniaturization of an imaging device employing SSIDs at a distal end of a catheter or other flexible umbilical can be accomplished. The invention accordingly provides a miniaturized imaging device, comprising a utility guide having at least one aperture configured for supporting utilities, an SSID including an imaging array carried by the utility guide, a lens optically coupled to the imaging array, and an umbilical. The imaging array can be on a top surface of the SSID, and a conductive element can be on a side surface of the SSID, wherein the imaging array is electrically coupled to the conductive element. The umbilical can include a conductive line that is carried by the at least one aperture, and the conductive line can be electrically coupled to the conductive element on the side surface of the SSID. In one embodiment, the conductive element can be a metal trace or conductive strip that is electrically coupled to the imaging array through a conductive pad. In another embodiment, the utility guide and the SSID can be a single integrated component.

An alternative miniaturized imaging device can comprise an SSID including, as an integral structure, an imaging array electrically coupled to a conductive pad, further including at least one utility aperture passing therethrough. To the imaging array, a lens can be optically coupled thereto. Further, an umbilical, including a conductive line, can be carried by the at least one aperture, and the conductive line can be directly electrically coupled to the conductive pad. In further detail, the electrical umbilical can be connected to the conductive element through a direct bonding joint, such as a solder joint, rather than wire bonding.

In either embodiment, the aperture (which is either present in the SSID itself, or alternative, in the utility guide) can carry a light source, a fluid irrigation or aspirator, or other device. Such other devices that can be carried by one or more aperture includes temperature sensors, force sensors, pressure sensors, fiber optics, microforceps, material retrieval tools, drug delivery devices, radiation emitting devices, laser diodes, electric cauterizers, and electric stimulators.

As these microcameras are very small, typically, a processor and a monitor remote from the SSID can be included, enabling real-time viewing of the image obtained by the SSID. These devices are typically attached to the microcamera via the umbilical. The umbilical can include a conductive line that provides functions such as power, ground, clock signal, and output signal.

The lens can be any lens that facilitates the collection of light or photons from an area around a distal tip of the microcamera. An example of a lens that can be used is a GRIN lens. Further, the lens can be optically coupled to the imaging array by direct contact, such as by an optically clear epoxy, or can have an intermediate optical insert interposed therebetween. Examples of such optical devices include a fiber optic line and/or a color filter insert configured for providing multiple colors from a monochromatic camera image, e.g., configured in a Bayer filter pattern.

With respect to the SSID, whether integrated with utility apertures or not, the SSID can be a CCD, a CID, or a CMOS imaging device.

In alternative embodiments, methods of operating a microcamera, such as for viewing within or beyond a small luminal opening, are provided. In a first method, steps can include (a) optically coupling a lens to an SSID; (b) defining a plurality of conductive paths, wherein at least one of the conductive paths is configured along multiple noncoplanar surfaces of the SSID; (c) powering the SSID through a first of the conductive paths; and (d) receiving signal from the SSID through a second of the conductive paths.

In a second method, steps can include (a) optically coupling a lens to an SSID including an imaging array; (b) powering the SSID through a first conductive path, wherein the first conductive path is defined by a first conductive umbilical wire, a first conductive pad, and a first bonding joint directly coupling a terminal end of the first conductive umbilical wire to the first conductive pad; and (c) transmitting signal from the imaging array for viewing along a second conductive path, wherein the second conductive path is defined by a second conductive pad, a second conductive umbilical wire, and a second bonding joint directly coupling the second conductive pad to a terminal end of the second conductive umbilical wire. By "directly coupling" by a "bonding joint," fragile wire bonding or bonding by means other than direct contact between the umbilical and the conductive pad is excluded. In one embodiment, the bonding joint can be a solder joint, solder bumping, eutectic bonding, electroplating, or conductive epoxy.

With respect to both of these methods, a further step of illuminating an area around the lens can be included. Additionally, the step of optically coupling can include the step of directly attaching the lens to an imaging array of the SSID, or alternatively, interposing an optical insert between the lens and an imaging array of the SSID. The defined conductive paths can be supplemented by additional conductive paths. In one embodiment, at least four conductive paths can be defined, such that ground and control of the SSID can supplement the power and signal requirements set forth above.

Additionally, a method of making an SSID in accordance with principles of the present invention can comprise the steps of (a) forming features within a predetermined area of a manufacture substrate having a thickness, wherein the features include a conductive pad electrically coupled to an imaging array; (b) removing portions of the manufacture substrate outside of the predetermined area such that the thickness outside the predetermined area is reduced, thereby forming an SSID attached to a thinned manufacture substrate, wherein the SSID has a top surface including the conductive pad, and a side surface adjacent to the top surface; (c) three-dimensionally masking the SSID such that the conductive pad and the side surface are exposed; and (d) applying a conductive material to the conductive pad and the side surface to electrically couple the conductive pad and the side surface.

The step of removing portions of the manufacture substrate can be accomplished by masking the predetermined area with a first photoresist material to protect the predetermined area from manufacture substrate removal. An additional step of removing the first photoresist material prior to the step of three-dimensionally masking the SSID can be carried out. A subsequent step of removing the SSID from the manufacture substrate after the conductive material has been applied can also be carried out. The step of three-dimensionally masking the SSID can be by using a second photoresist material. The second photoresist material can be the same material as the first photoresist material, or can be a different photoresist material. The method can also include the step of removing the second masking material after the step of applying the conductive material.

Alternatively, a method of making another SSID in accordance with embodiments of the present invention can comprise (a) forming features within a predetermined area of a manufacture substrate having a thickness, wherein the features include a conductive pad electrically coupled to an imaging array; (b) removing portions of the manufacture substrate outside of the predetermined area such that the thickness outside the predetermined area is reduced, thereby forming an SSID attached to a thinned manufacture substrate; (c) forming utility apertures through the SSID; and (d) removing the SSID from the thinned manufacture substrate.

Additional features and advantages of the invention will be apparent from the detailed description which follows, taken in conjunction with the accompanying drawings, which together illustrate, by way of example, features of the invention.

DETAILED DESCRIPTION OF THE PREFERRED EMBODIMENT(S)

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," or "SSID chip" in the exemplary embodiments generally comprises a substrate carrying an imaging array or pixel array for gathering image data, and can further comprise conductive pads electrically coupled to the imaging array, which facilitates electrical communication therebetween. In one embodiment, the SSID can comprise a silicon or silicon-like substrate or amorphous silicon thin film transistors (TFT) having features typically manufactured therein. Features can include the imaging array, the conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction. In some embodiments, the SSID can include utility apertures therethrough for carrying various utilities.

The term "umbilical" can include the collection of utilities that operate the SSID or the micro-camera as a whole. Typically, an umbilical includes a conductive line, such as electrical wire(s), for providing power, ground, clock signal, and output signal with respect to the SSID, though not all of these are strictly required. For example, ground can be provide by another means than through an umbilical wire, e.g., to a camera housing, etc. The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat. Thus, because of the differing refractive index in a radial direction from the optical axis, a lens of this shape can simulate the affects of a more traditionally shaped lens. Though GRIN lenses are generally shown in the FIGS., other lenses can also be used with the present invention, as is known by those skilled in the art.

With these definitions in mind, reference will now be made to the accompanying drawings, which illustrate, by way of example, embodiments of the invention.

Figure 1:
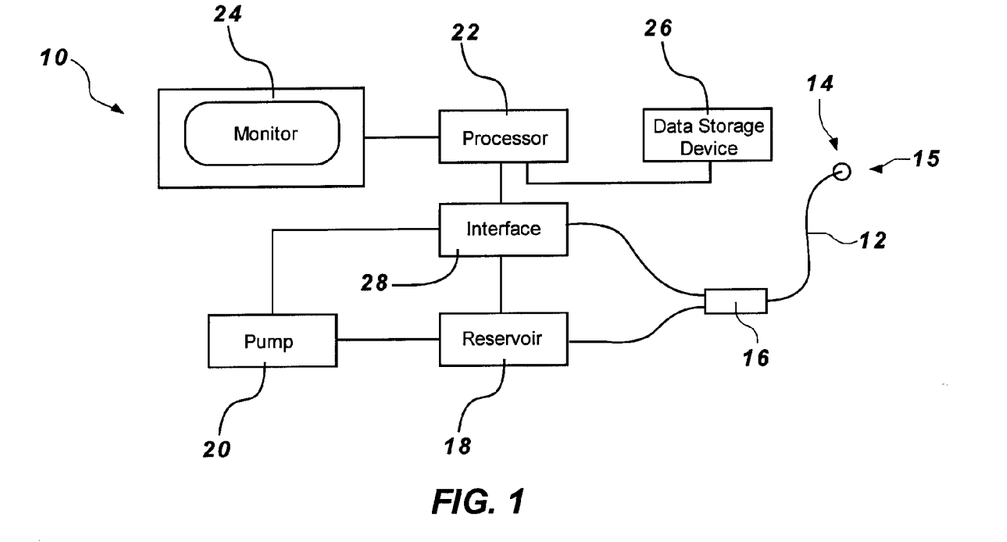
FIG. 1 is a schematic illustration of an exemplary medical imaging system in accordance with principles of the invention.
Figure 2:
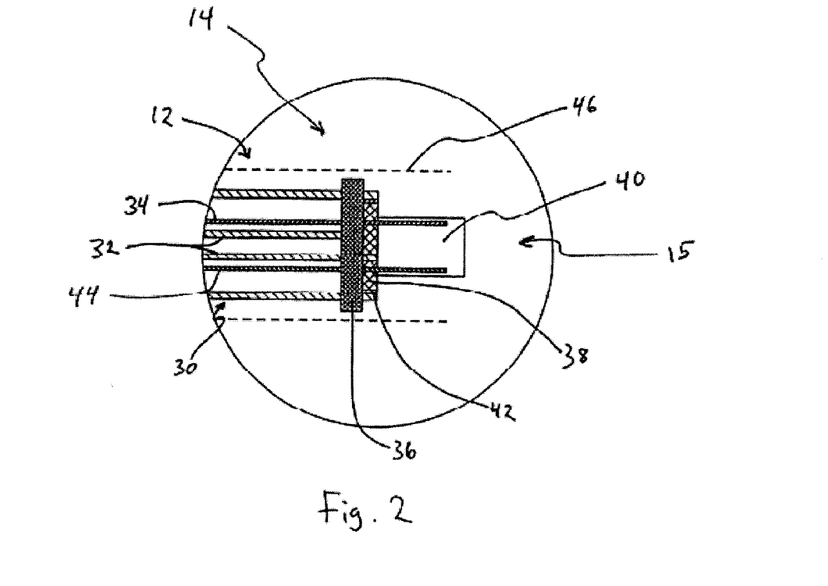
FIG. 2 is a side view of an exemplary embodiment of the present invention, which is an enlarged view of device 14 of FIG. 1.

With reference to FIGS. 1 and 2, the invention is embodied in a medical imaging system 10, including a catheter 12 having an imaging capability by means of an imaging device, shown generally at 14, at a distal tip 15 of the catheter. The system further includes a fitting 16 enabling an imaging fluid, such as a clear saline solution, to be dispensed to the distal tip portion of the catheter from a reservoir 18 to displace body fluids as needed to provide a clearer image. A pump 20 is provided, and is manually actuated by a medical practitioner performing a medical imaging procedure, or can be automated and electronically controlled so as to dispense fluid on demand according to control signals from the practitioner, sensors, or according to software commands.

A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device 14 and feeds a digital image signal to the processor based on a signal received from the imaging device via an electrical umbilical 30, including conductive wires 32, a fluid dispenser 34, and a light source 44, through the catheter 12. The interface can also be configured to control the pump 20 based on control signals from the processor or a medical practitioner performing an imaging procedure.

With more specific reference to FIG. 2, the imaging device 14 at the distal tip 15 can include a utility guide 36 for supporting or carrying the umbilical 30, which can include electrical wires 32, fluid dispenser 34, and a light source 44. Other components that can be carried by the utility guide can include, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators. The utility guide can also carry an SSID or solid state imaging device 38 that includes an imaging array (not shown) and conductive pads 42 for coupling the electrical wires to the SSID. Though the utility guide and the SSID are shown as two separate units, it is understood that a single integrated unit can also be fabricated. The light source shown is a fiber optic carried by the utility guide. However, other light sources can be used, such as those carried by the SSID. For example, the SSID can also include light-emitting diodes (LEDs) configured to illuminate the area immediately adjacent the distal tip portion. With the SSID in this configuration, a GRIN lens 40 is shown optically coupled to the imaging array of the SSID.

If a GRIN lens 40 is used, the lens can be substantially cylindrical in shape. In one embodiment, the GRIN lens can have a first flat end for receiving light, a second flat end for passing the light to the imaging array, and an outer curved surface surrounded by an opaque coating or sleeve member to prevent unwanted light from entering the GRIN lens. The GRIN lens can be optically coupled to the imaging array by direct contact between the second flat end and the imaging array of the SSID 38. Such direct contact can include an optically transparent or translucent bonding material at the interface between the second flat end and the imaging array. Alternatively, the GRIN lens can be optically coupled to the imaging array of the SSID through an intermediate optical device, such as a fiber optic or a color filter, or any shape optical lens such as a prism or wide angle lens.

The catheter 12 can be configured to be bendable and flexible so as to be steerable within a patient's anatomy and to minimize trauma. For example, the catheter can comprise a micromachined tube 46 at the distal tip portion, and cut-out portions (not shown) can allow for increased flexibility of the tube, and also allow for outflow of an imaging fluid to displace body fluids in the immediate area of the distal tip portion for more clear imaging. Such a micromachined tube can also allow bending to facilitate guiding the catheter to a desired location by selection of desired pathways as the catheter is advanced.

The catheter 12 can comprise an internal tensionable wire adjacent one side of the distal tip portion, which when tensioned, causes the distal tip portion 15 to deflect as is known in the art. A combination of deflection and rotation of the distal tip portion of the catheter provides steerability of the device. Another alternative for directability of the distal tip portion is to provide a micro-actuator (not shown) such as an element which expands or contracts upon application of an electrical current signal. Such an element can be substituted for the tension wire, for example.

As will also be appreciated, while the system is illustrated by the exemplary embodiment of a medical imaging system, these arrangements could be used in other devices, such as visual sensors in other devices, surveillance apparatus, and in other applications where a very small imaging device can be useful.

Moreover, with reference to all of the embodiments described herein, the device contemplated can be very small in size, and accordingly the imaging array of the SSID can have a lower pixel count than would otherwise be desirable. As technology advances, pixel size can be reduced, thereby providing clearer images and data. However, when using a lower number of pixels in an imaging array, the resolution of the image provided by the device can be enhanced through software in processing image data received from the SSID. The processor showing in FIG. 1, can be appropriately programmed to further resolve a scanned image from an array of an SSID, for example, based on information received as the SSID is moved slightly, such as from vibration controlled vibration. The processor can analyze how such image data from the imaging array is altered due to the vibration, and can refine the image based on this information.

Figure 3:
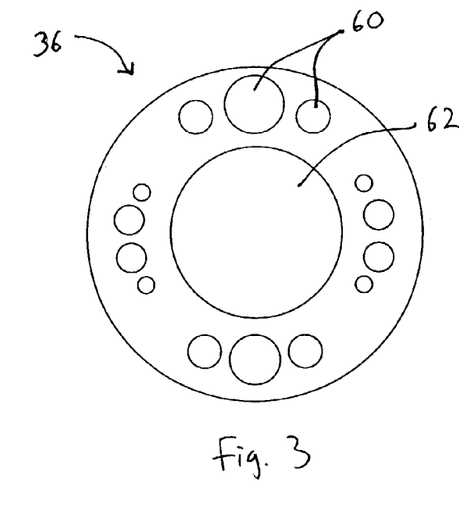
FIG. 3 is a top plan view of a utility guide that can be used in accordance with embodiments of the present invention.

Referring to FIG. 3, an embodiment of a utility guide 36 is shown. The utility guide includes a plurality of utility apertures 60 and a central aperture 62. The utility guide can be of any material that will not interfere with the function of the SSID (not shown). For example, the utility guide can be of silicon that has been deep reactive ion etched to form the desired structure. Alternatively, a polymeric material such as SU-8 polymer material manufactured by IBM, Foturan which is a photosensitive glass by Corning, or polymethyl methacrylate (PMMA) molded by Lithographie Galvanoformung Abformung (LIGA) can also be used for forming such a structure. The utility guide has the dual function of carrying the SSID, as well as carrying the utilities provided by the umbilical.

Figure 4:
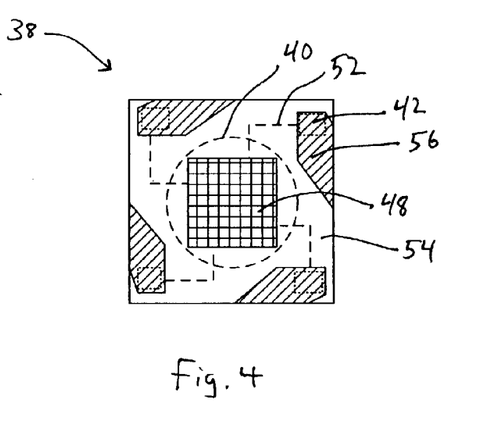
FIG. 4 is a top plan view of an SSID that can be used in accordance with embodiments of the present invention.

FIG. 4 depicts an embodiment of an SSID 38 that can be used in accordance with embodiments of the present invention. The SSID includes an imaging array 48 electrically coupled to conductive pads 42 by an electrical connection 52. All of these features 48, 42, 52 are manufactured into a substrate 54 when the SSID is prepared. Additionally, a conductive strip or metal trace 56 is present on the SSID, providing electrical communication between the conductive pads and respective side surfaces (not shown) of the SSID. The positioning of a GRIN lens 40 with respect to the imaging array is also shown.

Figure 5:
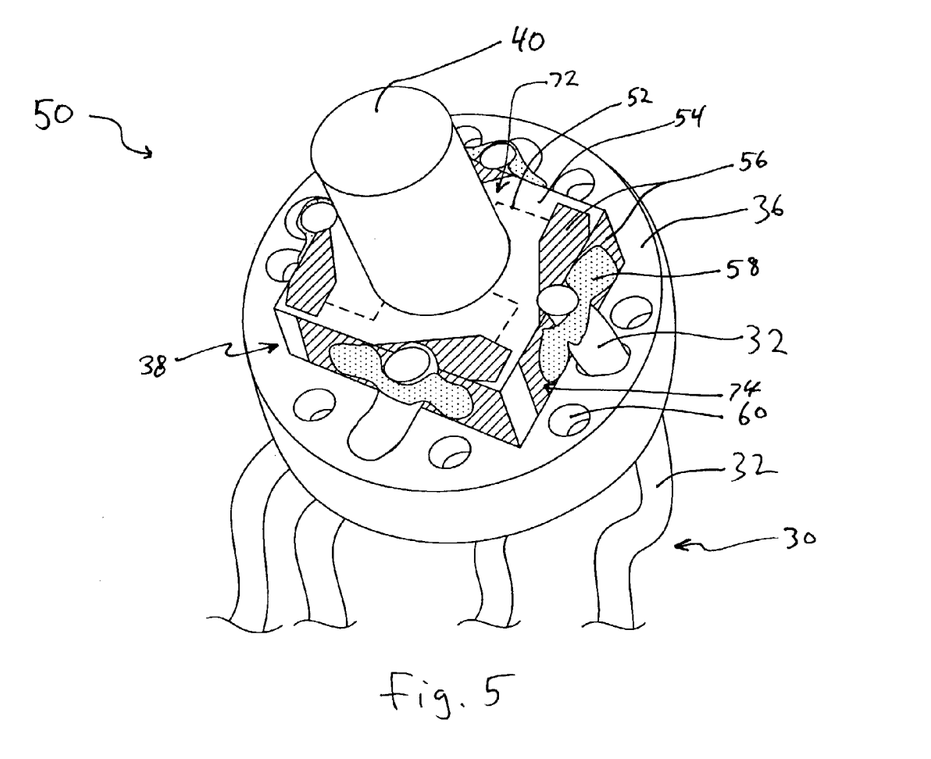
FIG. 5 is a perspective view of an exemplary microcamera of the present invention that utilizes the utility guide of FIG. 3 and the SSID of FIG. 4.

FIG. 5 depicts an assembled microcamera 50 that utilizes the utility guide 36 of FIG. 3 and the SSID 38 of FIG. 4. The utility guide includes utility apertures 60 and a central aperture (not shown). The SSID is carried by the utility guide, and can be bound to the utility guide by an epoxy material, anodic bonding, or eutectic bonding. Alternatively, the utility guide can be micromachined by a deep reactive ion etch (DRIE) process by utilizing the SSID as a staring material, and thus, removing the additional step of connecting the utility guide to SSID. The SSID includes conductive strip 56 that provides conductivity from a top surface 72 of the SSID to a side surface 74 of the SSID. Thus, conductive wires 32 of the umbilical 30 can be carried by a utility aperture of the utility guide, and attached to the conductive strip by a bonding joint 58, such as a solder joint, at the side surface. The solder joint can be of a conductive bonding material, such as silver or gold filled epoxy, silver or gold solder, or another suitable adhesive or eutectic conductive substance. Alternatively, the connection between conductive strip and the conductive wires can be through wire bonding, solder bumping, eutectic bonding, electroplating, or conductive epoxy. However, with this configuration, a direct bonding joint having no wire bonding between the conductive strips and the conductive wires can be preferred, as good steerability can be achieved with less risk of breaking electrical bonding. As the conductive strip is electrically coupled to the conductive pads (not shown), and as the conductive pads are electrically coupled to the imaging array (not shown) by an electrical connection 52, electrical coupling between the imaging array and the conductive wires of the umbilical is effectuated.

The SSID can be any solid state imaging device, such as a CCD, a CID, or a CMOS imaging device. The substrate 54 of the SSID 38 can comprise a silicon or silicon-like material or can be an amorphous silicon thin film transistors (TFT) having features typically manufactured therein. Features can include the imaging array (not shown), the conductive pads (not shown), and conductive strips or metal traces 56 (which are typically applied topically after SSID foundry manufacture). Other integrated circuit components can also be present for desired applications, such as light emitting diodes (LEDs) (not shown) for providing light to areas around the lens. As the above described component are exemplary, it is not required that all of these components be present, as long as there is a visual or photon data gathering means, and some means of converting that data to a visual image or a visual reconstruction.

The conductive wires 32, can provide the dual function of guiding the direction the SSID, such as by tensioning, as well as provide electrical contact between any power source/signal processors (not shown) and the SSID, though this dual functionality is not required. Alternatively, steering can be by a micromachined tube, as is known in the art. An example of such micromachined tubing is described in U.S. Pat. No. 6,428,489, which is incorporated herein by reference. In further detail with respect to the umbilical, the conductive wires of the umbilical can provide power, ground, clock signal or control, and output signal to the SSID. Further, the electrical umbilical 30, including conductive wires, can comprise an insulator coating portion around each individual utility, and/ or around the umbilical as a whole.

The lens 40, SSID 38, and utility guide 36 of the microcamera can be fused together or bonded together as desired. For example an epoxy, such as a UV cure epoxy, can be used to bond the lens to the imaging array 48 of the SSID. Likewise, an epoxy can also be used to bond the utility guide to the SSID. However, with the use of such epoxy, care should be taken not use a UV light at an intensity that would damage the SSID or other structures of the device.

Figure 6:
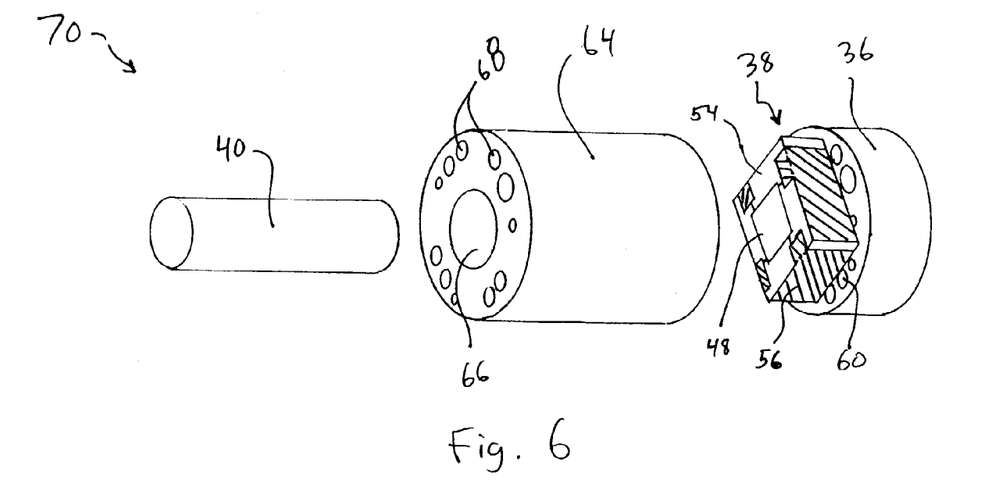
FIG. 6 is an exploded perspective view of another exemplary embodiment of the present invention.
Figure 7:
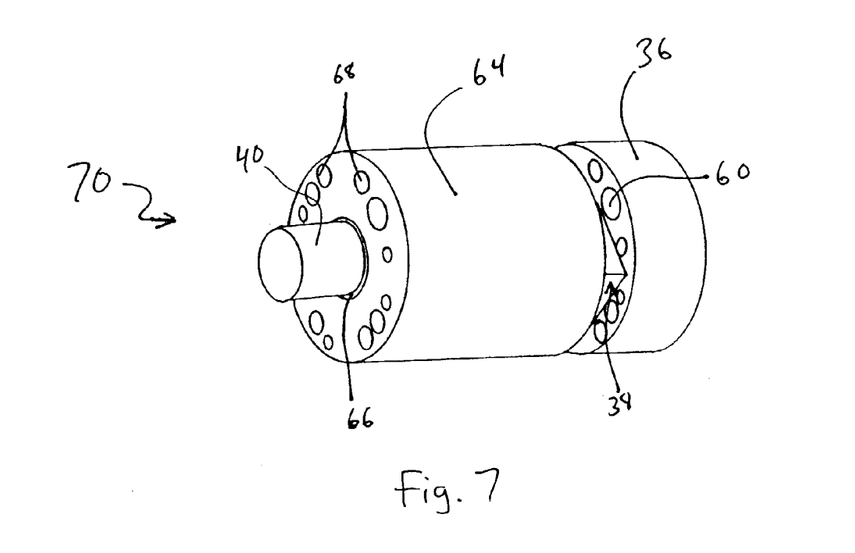
FIG. 7 is an assembled perspective view of the exemplary embodiment of FIG. 6.

FIGS. 6 and 7 depict an alternative microcamera assembly 70 wherein the lens 40 is held in place by a lens holder 64. The lens holder can include utility apertures 68 for carrying or guiding utilities, such as light or fluid aspirators/dispensers. The lens holder also includes a lens aperture 66 for supporting the lens. If the lens is a GRIN lens, the lens can be coated with an opaque coating or sleeve on or around the curved surface to prevent light from entering the lens at other than the flat surface that is most distal with respect to the SSID. The lens holder can act, in part, as the opaque sleeve that prevents unwanted light from entering the side, provide the lens holder is fabricated from an opaque material.

The SSID 38 and utility guide 36 are configured similarly as that described with respect to FIG. 5. Specifically, the SSID includes a substrate 54 carrying an imaging array 48 and conductive strips or metal traces 56. The utility guide 36 includes utility apertures 60 that are aligned with the utility apertures 68 of the lens holder 64. Utilities, such as conductive wires (not shown), that are used to power and carry signal with respect to the SSID, need not be carried by the utility apertures of the lens holder, as such conductive wires usually terminate at the SSID. The utility apertures of the lens holder are primarily for carrying utilities that are used at or near the lens, e.g., fluid dispensers/aspirators, light utilities, forceps, and the like.

Figure 8:
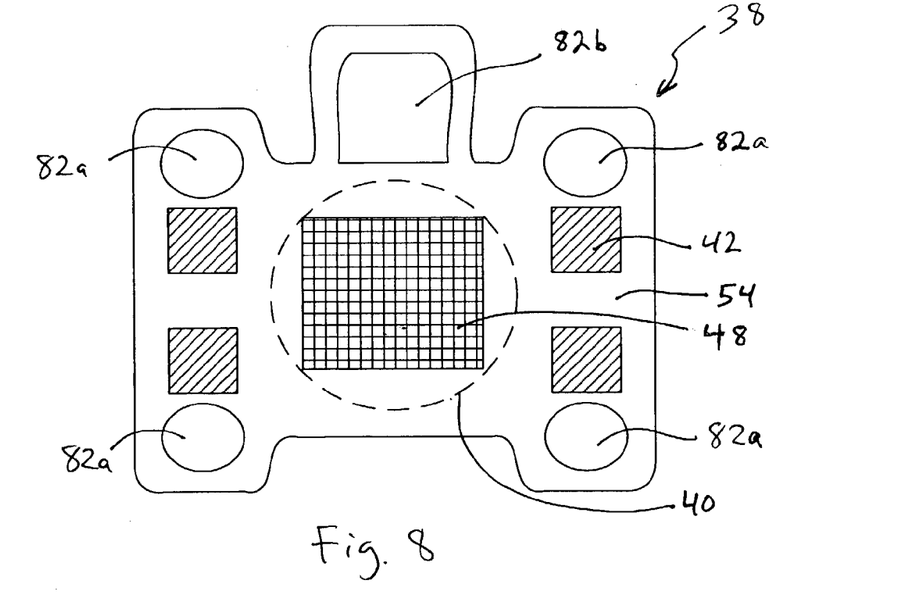
FIG. 8 is a top plan view of an SSID integrated with utility apertures in accordance with another exemplary embodiment of the invention.

Turning now to FIG. 8, an alternative SSID 38 that is integrated with utility apertures 82a, 82b is shown. The SSID includes a substrate 54 that carries conductive pads 42 and an imaging array 48 fabricated therein. As the SSID includes five utility apertures 82a, 82b, various utilities can be carried by the SSID device without the use of a separate utility guide as described with respect to FIG. 5. Lens 40 is shown as it can be positioned with respect to the imaging array.

Figure 9:
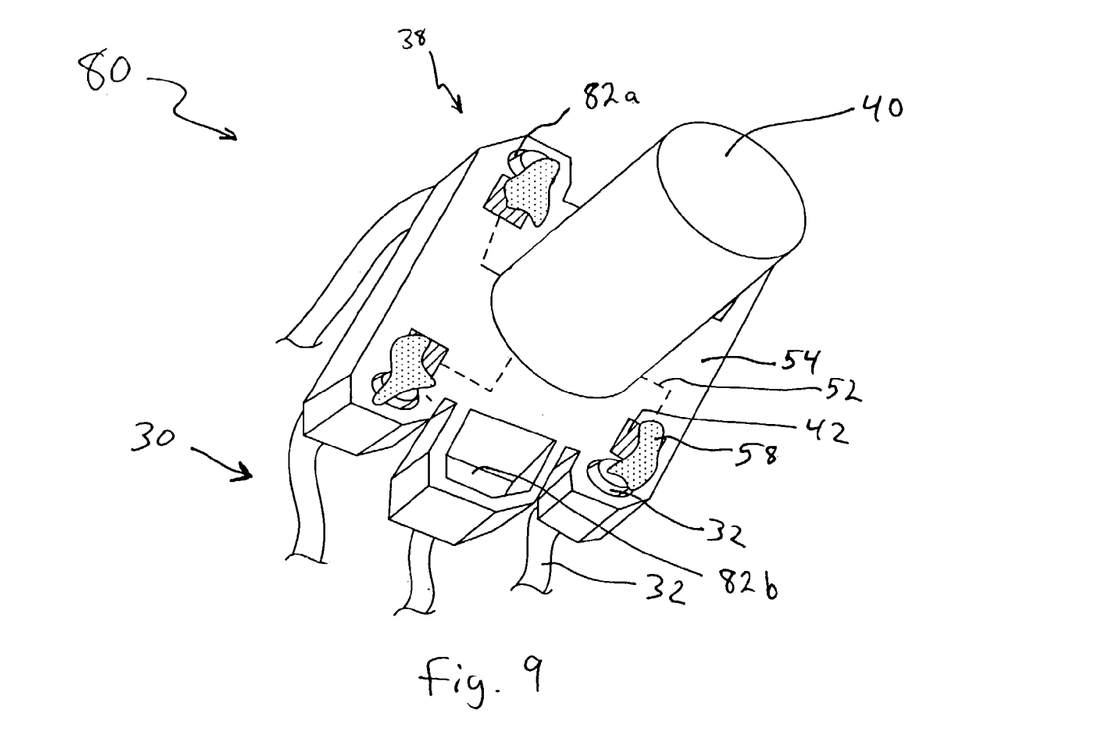
FIG. 9 is a perspective view of an exemplary microcamera of the present invention that utilizes the SSID of FIG. 8.

FIG. 9 depicts a system 80 that utilizes the SSID 38 of FIG. 8. In this embodiment, the SSID includes a substrate 54, which carries an imaging array (not shown), conductive pads 42, and electrical connections 52 between the imaging array and the conductive pads. The SSID is electrically coupled to an umbilical 30 at the conductive pads 42. Specifically, conductive wires 32 of the umbilical are carried by four utility apertures 82a and electrically coupled to the conductive pads 42 by respective solder joints 58. The four conductive wires can be used to provide power, ground, clock signal to the SSID, as well as image signal from the SSID to a remote processor/monitor device (not shown). Only four of the five apertures are used to carry the conductive wires. The larger fifth aperture 82b can carry other utilities such as light sources, fluid aspirators and/or dispensers, temperature sensors, force sensors, pressure sensors, fiber optics, microforceps, material retrieval tools, drug delivery devices, radiation emitting devices, laser diodes, electric cauterizers, and electric stimulators, and the like. The fifth aperture 82b can also carry multiple utility devices, or additional apertures (not shown) can be included in the SSID for carrying separate utilities. Lens 40 can be positioned with respect to the SSID to be optically coupled to the imaging array. All of the disclosure related to the lens, SSID, umbilical, apertures, and the like, described in other embodiments, such as in FIG. 5, can also be applicable to this embodiment as well.

Figure 10:
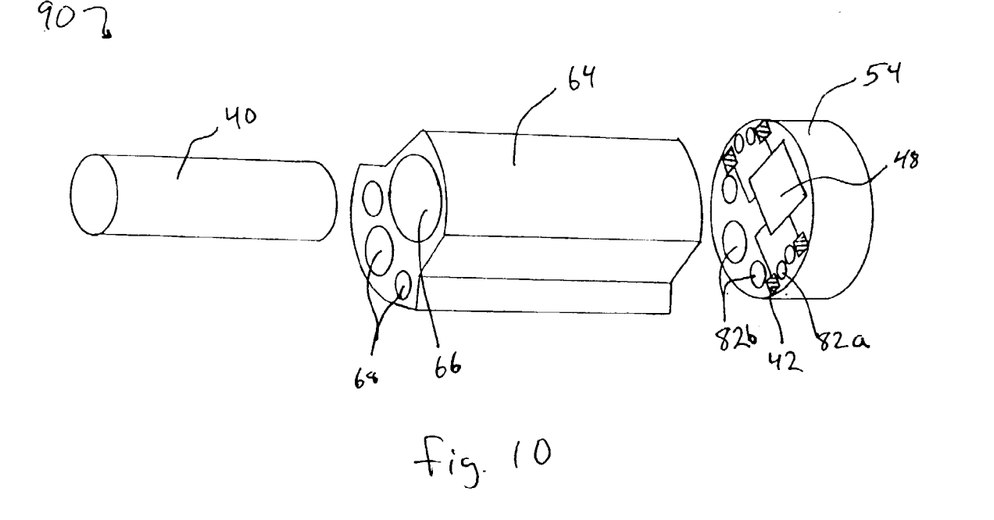
FIG. 10 is an exploded perspective view of another exemplary embodiment of the present invention.
Figure 11:
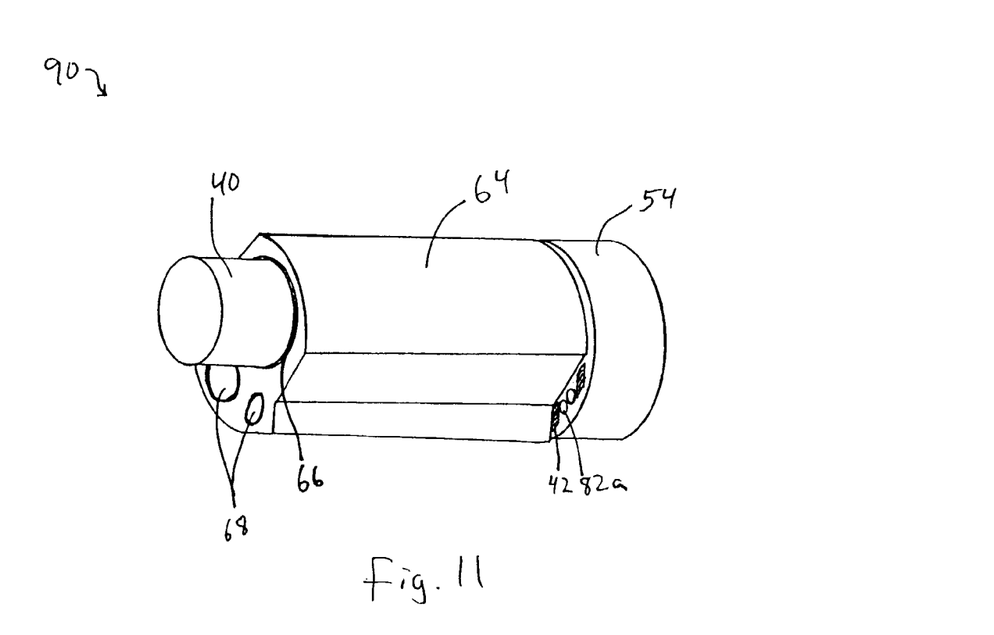
FIG. 11 is an assembled perspective view of the exemplary embodiment of FIG. 10.

FIGS. 10 and 11 depict an alternative microcamera assembly 90 wherein the lens 40 is held in place by a lens holder 64. As with FIGS. 6 and 7, the lens holder can include utility apertures 68 for carrying or guiding utilities. The lens holder can also include a lens aperture 66 for supporting the lens. Like the SSID shown in FIG. 8, the SSID includes conductive pads 42, utility apertures 82a, 82b, and an imaging array 48, all as an integrated unit. Utilities, such as conductive wires (not shown), that are used to power and carry signal with respect to the SSID, need not be carried by the utility apertures of the lens holder. The utility apertures of the lens holder are primarily for carrying utilities that are used at or near the lens. When the lens holder is in place with respect to the SSID, as shown in FIG. 11, utility apertures 82a and conductive pads 42 are exposed, thereby providing a means for carrying conductive wires (not shown) for attachment to the conductive pads, without interference from the lens holder.

Figure 12:
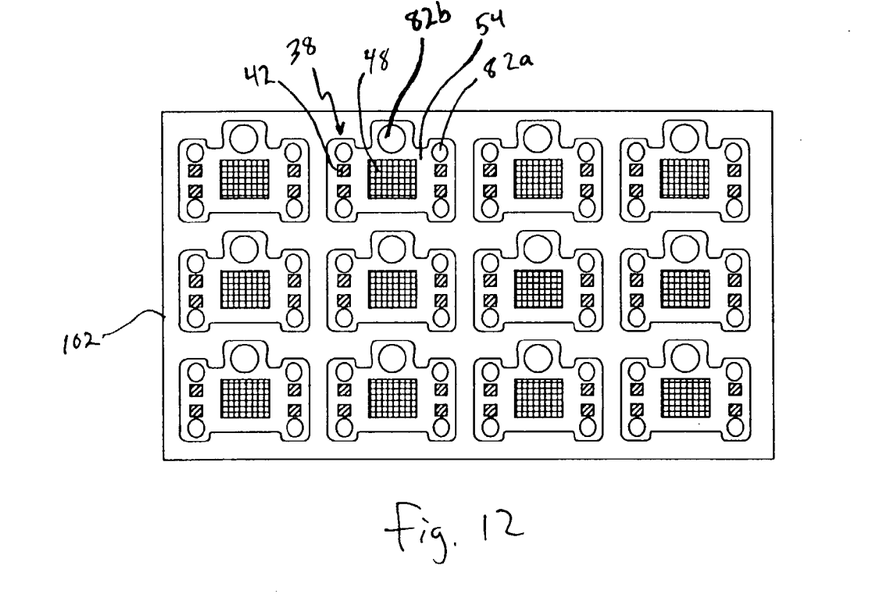
FIG. 12 is a top plan view of a plurality of SSIDs on a common substrate at a stage of the manufacturing process.
Figure 13:
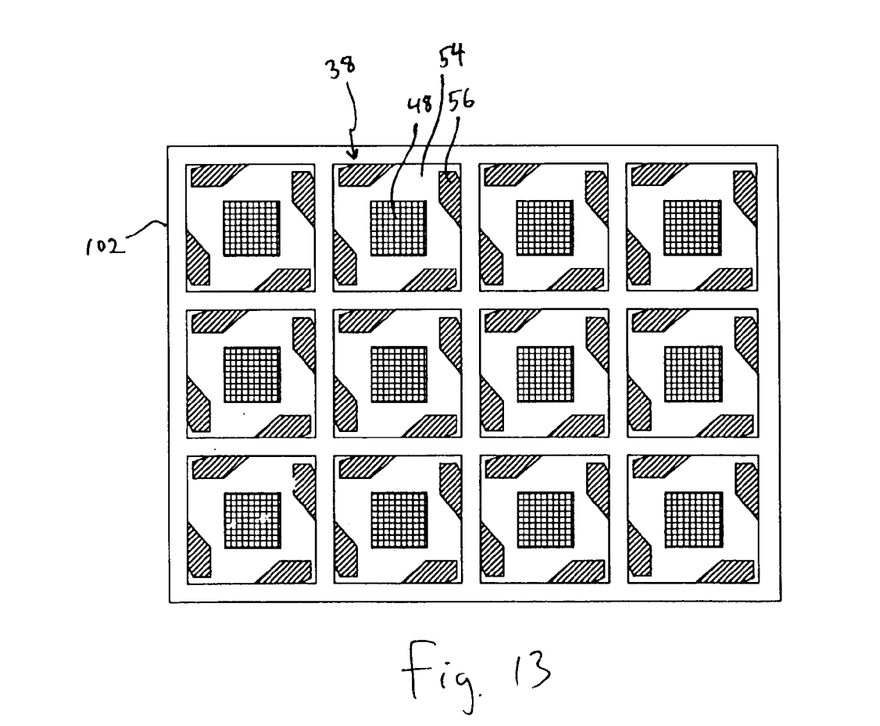
FIG. 13 is a top plan view of an alternative embodiment of a plurality of SSIDs on a common substrate at a stage of the manufacturing process.

FIGS. 12 and 13 provide schematic representations of a preparative step in creating a plurality of SSIDs 38 on a common substrate 102. FIG. 12 depicts the mass preparation of the SSID of FIG. 8, and FIG. 13 depicts the mass preparation of the SSID of FIG. 4. Both preparative schemes provide a means of preparing SSIDs including a substrate 54 having an imaging array 48 and conductive pads 42 fabricated thereon. FIG. 12 further includes apertures 82a, 82b configured in the SSID itself. FIG. 13 does not shown the conductive pads as they are not viewable due to the presence of conductive strips 56.

Turning now to the specifics of how an SSID can be manufactured, FIGS. 14a to 14e depict one possible embodiment. This process is described as exemplary, as one SSID can be made individually, or alternatively, many more that the four SSIDs depicted can be manufactured together, either by the process described below or by other known chip manufacturing processes. Preliminarily, a VLSI design can be sent to a manufacturing CMOS foundry, wherein a plurality of "chips" or feature groupings 88 can be manufactured on a single silicon manufacture substrate 102. The individual feature groupings on the manufacture substrate can then be processed and separated to form individual SSIDs.

Figure 14A:
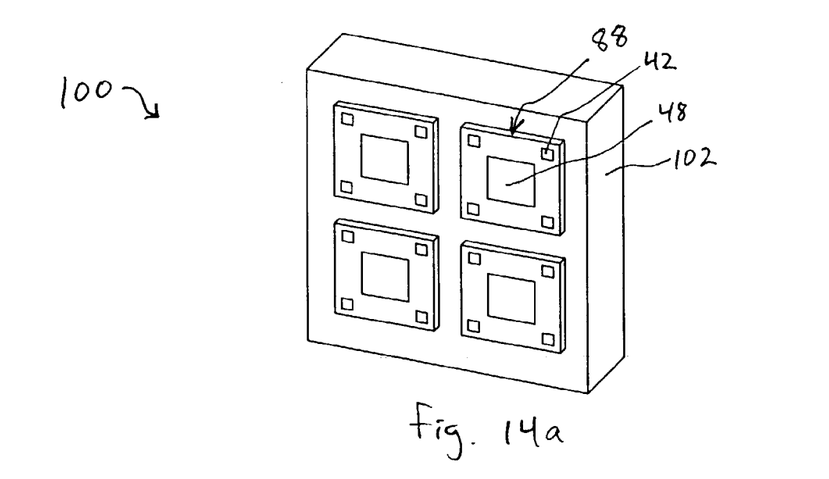
FIGS. 14a to 14e provides perspective schematic representations of the manufacturing process in accordance with an embodiment of the present invention.

FIG. 14a depicts a manufacture substrate 102 carrying a plurality of feature grouping 88 (each feature grouping individually becoming individual SSIDs). The individual feature groupings include an imaging array 48, conductive pads 42, and other circuitry components (not shown). Once received from the foundry, typically, the substrate as a whole is coated with oxy-nitride, silicon dioxide, or the like. Reactive ion etching (RIE) can be carried out to remove this protective coating and all of the other thin film layers, so that it is left with a bare silicon top surface.

Figure 14B:
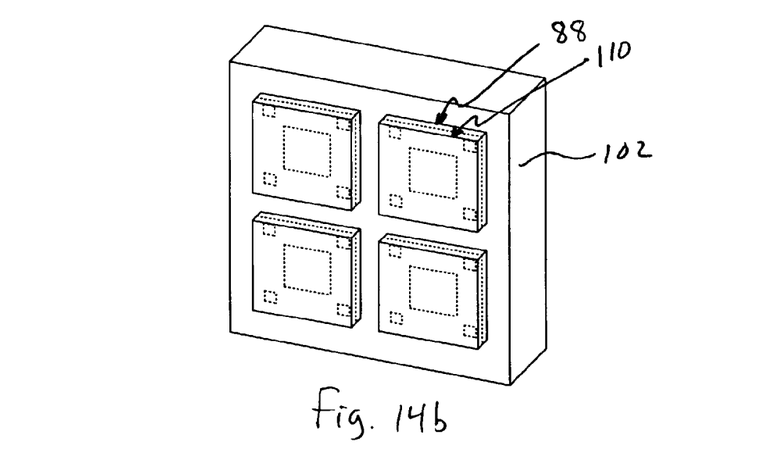
Figure 14C:
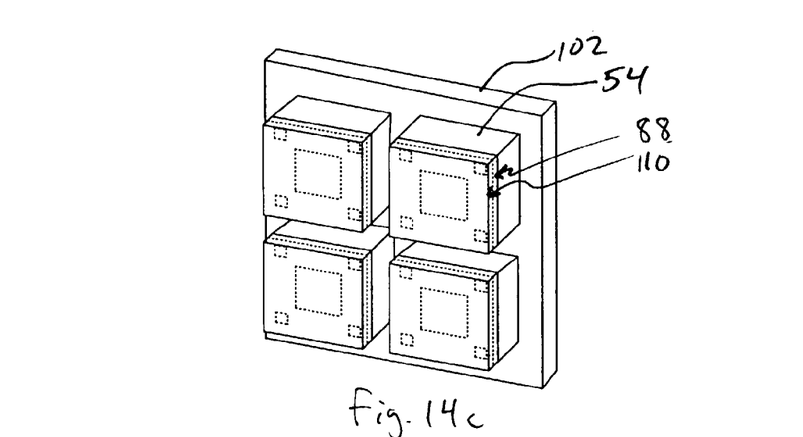

Referring to FIG. 14b, each individual feature grouping 88 can be coated with a photoresist material 110 to protect the area of interest from subsequent separation steps. In one embodiment, the photoresist can be applied at a thickness of about 10 microns. Referring to FIG. 14c, the unprotected areas, i.e., areas between each individual feature grouping, can then be etched away by processes known in the art, such as deep reactive ion etching processes. Etching can be carried out until manufacture substrate 102 becomes thinned, and the SSID substrate 54 becomes exposed (which is of the same material as the manufacture substrate). An exemplary thickness for the thinned manufacture substrate is about 50 microns.

Figure 14D:
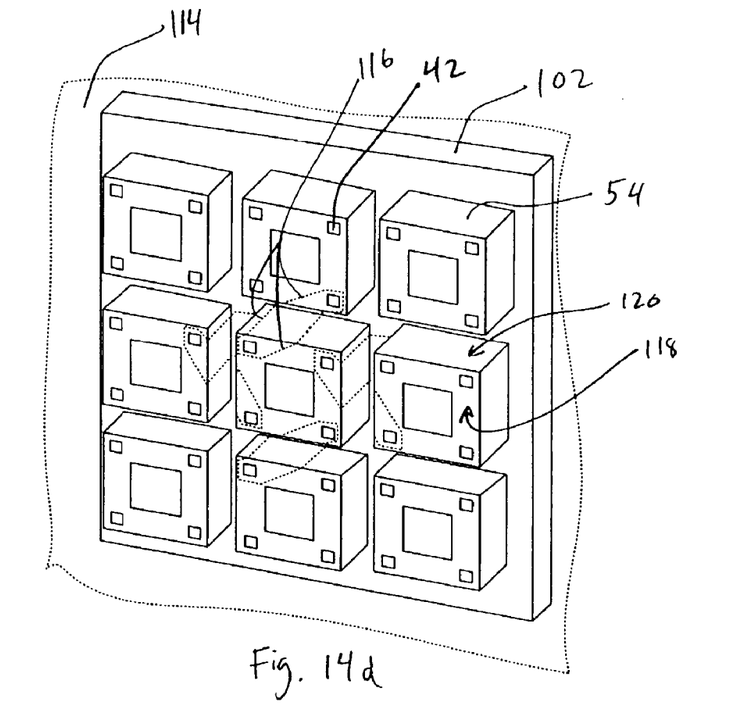
Figure 14E:
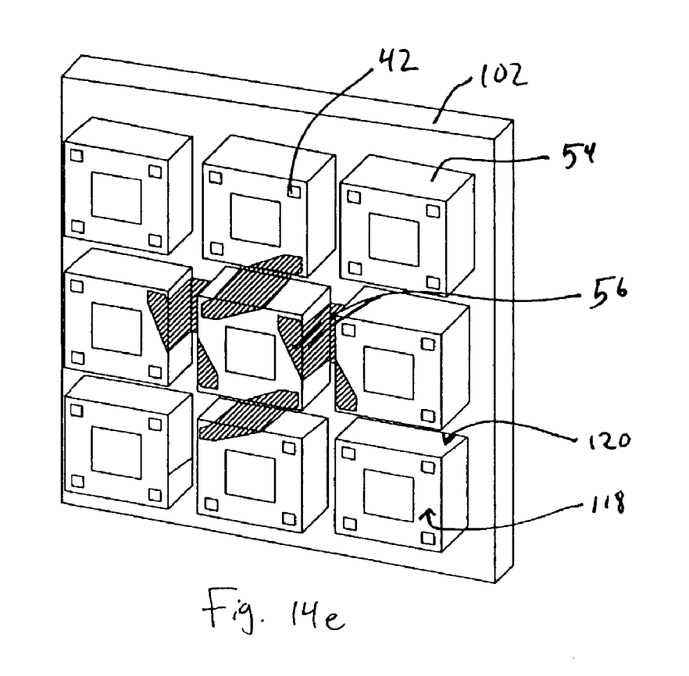

FIGS. 14d and 14e depict three by three arrays (rather than two by two arrays shown in FIGS. 14a to 14c) of SSIDs in order to show how a single SSID is masked and coated with conductive strips. Masking and metallizing of only one complete SSID (in the middle of the array) is shown, though processing would typically occur on all SSIDs present on the array. Additionally, before masking, the photoresist material is removed, and then 1.5 microns of silicon dioxide (not shown) is deposited on the SSID array and manufacture substrate 102 using a Plasma Enhanced Chemical Vapor Deposition process. Reactive ion etching (RIE) can then be used to remove the silicon dioxide from the conductive pads (not shown). Once the etching is complete, the conductive pads are uniquely exposed, and the array of SSIDs on the thinned manufacture substrate is prepared to be masked.

FIG. 14d depicts a photomask 114 having a plurality of cutouts 116. The photomask is applied as a three-dimensional structure such that a top surface 118 and a side surface 120 of each SSID can be partially exposed at desired areas only. In other words, the photomask is applied onto the three-dimensional array of SSIDs, and is patterned such that portions of the side surfaces and top surface of each SSID can be selectively metallized, including at the location of the exposed conductive pads. Once masked, metallization can be accomplished by a sputtering process such that exposed surfaces of each individual SSID are coated. For example, sputtering of Ti/Pt via a lift off process can be used for metallization.

Resulting from this process, and as depicted in FIG. 14e, each of four side surfaces of each SSID is transformed to include conductive strips 56 that electrically couples a side surface of the SSID to a top surface of the SSID (where the conductive pads are present for controlling the imaging array). Reactive ion etching (RIE) can then be used again to remove the silicon manufacture substrate 102, thereby separating each individual SSID from the manufacture substrate.

Other SSIDs in accordance with embodiments of the present invention can also be made using similar procedures. For example, the SSID shown in FIG. 8 can be made similarly as that described above, except that the three-dimensional masking step shown in FIG. 14d is not necessary, as there is no "around the corner" metal trace present. Additionally, an added step of boring utility apertures through the SSID can be carried out by drilling, masking (as in FIG. 14b) to enable etching away of the apertures, or some other known procedure.

Figure 15:
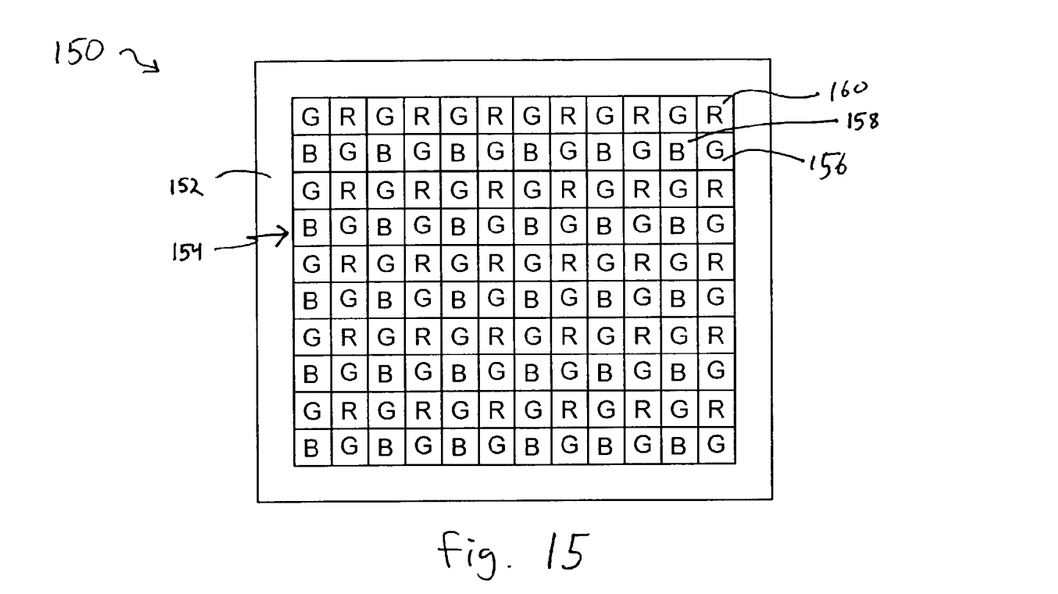
FIG. 15 is plan view along the optical axis of an exemplary color filter insert that can be used with imaging devices in accordance with principles of the invention.
Figure 16:
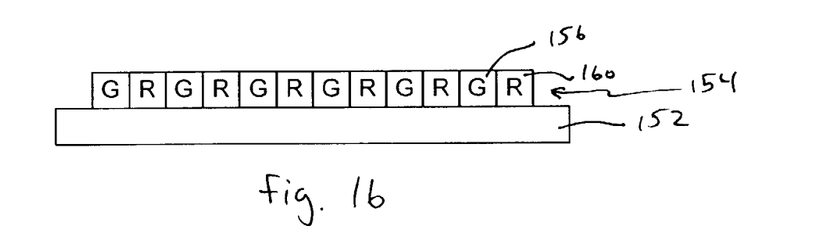
FIG. 16 is a side view of the color filter insert of FIG. 15.
Figure 17:
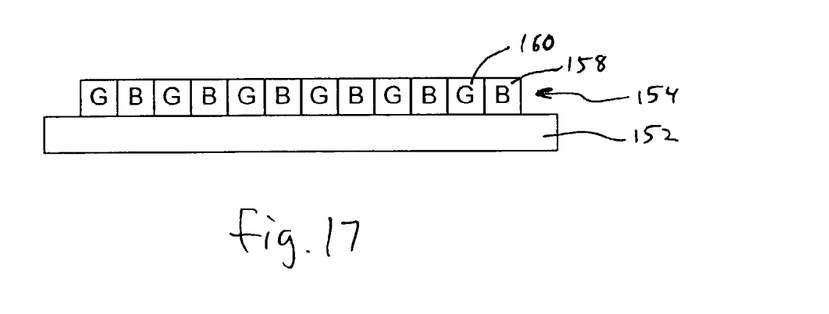
FIG. 17 is a second side view of the color filter insert of FIG. 15, taken at 90 degrees with respect to FIG. 16.

Specifically, with reference to FIGS. 15-17, a color filter insert, shown generally at 150, can comprise a substantially optically clear filter substrate 152 and a color filter mosaic portion 154. The filter insert as a whole is made up of green transparent color material 156, blue transparent color material 158, and red transparent color material 160. Each of the transparent color material 156, 158, 160 can be polymerized color resins such as those available from Brewer Science. In one embodiment, the green color material 156 can be put down on the clear filter substrate first, then the red 160 and blue 158 color material can be positioned in the appropriate spaces provided by the green material. Each transparent color material can be configured to be the size of an SSID image array pixel. The optically clear filter substrate can be, for example, a polymeric material such as SU-8 available from IBM, having a thickness of about 20 microns, though other thickness can be used.

Figure 18:
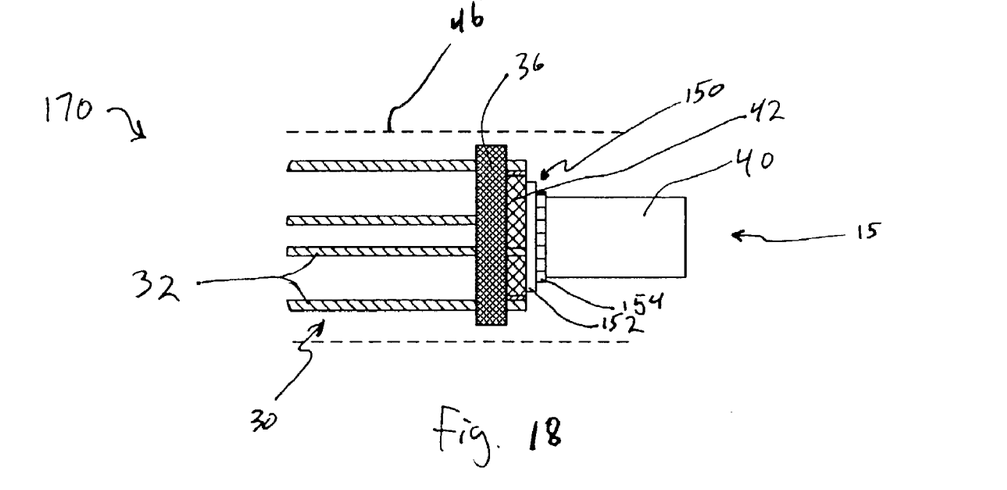
FIG. 18 is a schematic side view representation of another exemplary embodiment having a color filter insert of FIG. 15 inserted therein.
Figure 19:
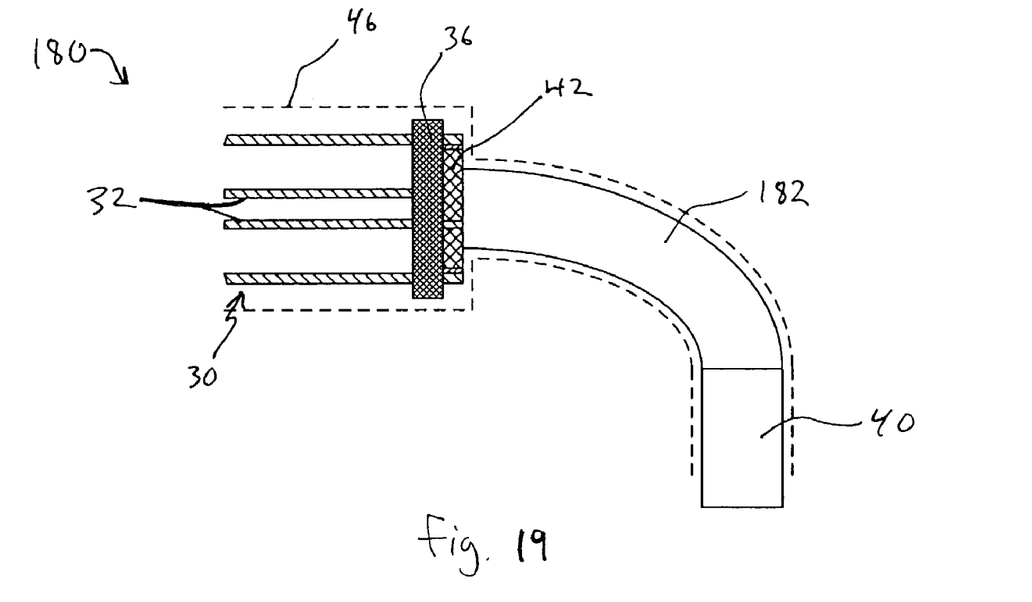
FIG. 19 is a schematic side view representation of another exemplary embodiment having a fiber optic inserted therein.

Turning now to FIG. 18, a system 170, including a color filter insert having an optical clear filter substrate 152 and the color filter mosaic portion 154, can be positioned between a lens 40 and an imaging array (not shown) of an SSID 38. FIG. 19 depicts an alternative system 180, wherein a fiber optic 182 is used to optically couple a lens 40 with an imaging array (not shown) of an SSID 38. Any bonding technique or mechanical coupling can be used to connect the SSID to the lens through the color filter insert or fiber optic in order to make the optical connection, such as bonding by a clear bonding epoxy. In both FIGS. 18 and 19, as described previously, the imaging device at the distal tip 15 can include a utility guide 36 for supporting or carrying the umbilical 30, which can include an electrical wires 32 and other utilities (not shown). Both FIGS. 18 and 19 also depict micromachined tubing 46 to support and direct the camera.

As will be appreciated, an imaging device in accordance with principles of the invention can be made very small, and is useful in solving certain imaging problems, particularly, that of imaging a remote location distal of a small opening, for example in human anatomy distal of a small orifice or luminal space (anatomical or artificial, such as a trocar lumen), or via a small incision, etc., the configuration facilitates miniaturizations, and simplifies assembly. In fact, because of the solid state nature of the SSID, and because of the use of the GRIN lens, these cameras can be made to be micron-sized for reaching areas previously inaccessible, such as dental/orthodontics, fallopian tubes, heart, lungs, vestibular region of ear, and the like. Larger lumens or cavities can be view with a greater degree of comfort and less patient duress, including the colon, stomach, esophagus, or any other similar anatomical structures. Additionally, such devices can be used for in situ tissue analysis.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A miniaturized imaging device, comprising:
    (a) a utility guide having at least one aperture configured for supporting utilities, said utility guide comprising a substantially planar surface oriented perpendicular to a longitudinal axis of the miniaturized imaging device;
    (b) a solid state imaging chip disposed on the planar surface of the utility guide;
    (c) an imaging array disposed on a top surface of said imaging chip and a conductive element on a side surface of said imaging chip, said imaging array being electrically coupled to the conductive element;
    (c) a lens optically coupled to the imaging array;
    (d) an umbilical, including a conductive line, carried by the at least one aperture, said conductive line electrically coupled to the conductive element on the side surface of the imaging chip; and
    (e) a lens holder disposed about the lens, said lens holder comprising at least one aperture, wherein the at least one aperture of the lens holder is collinear with the at least one aperture of the utility guide, and wherein the at least one aperture of the lens holder is perpendicular to a light receiving surface of the imaging array.

2. A miniaturized imaging device as in claim 1, wherein the conductive element is a metal trace, said metal trace being electrically coupled to the imaging array through a conductive pad on the top surface.

3. A miniaturized imaging device as in claim 1, wherein the utility guide and the imaging chip are a single integrated component.

4. A miniaturized imaging device as in claim 1, wherein the conductive line is connected to the conductive element through a direct bonding joint rather than wire bonding.

5. A miniaturized imaging device as in claim 1, further comprising a light source carried by the utility guide.

6. A miniaturized imaging device as in claim 1, wherein the utility guide is configured to carry at least one member selected from the group consisting of electrical wires, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators.

7. A miniaturized imaging device as in claim 1, further comprising a processor and a monitor remote from the imaging device, enabling real-time viewing of an image obtained by the imaging device.

8. A miniaturized imaging device as in claim 1, wherein the conductive line of the umbilical includes power, ground, clock signal, and output signal.

9. A miniaturized imaging device as in claim 1, further comprising an optical insert positioned optically between the lens and the imaging array.

10. A miniaturized imaging device as in claim 9, wherein the optical insert is a color filter insert configured for providing multiple colors from a monochromatic camera image.

11. A miniaturized imaging device, comprising:
(a) a solid state imaging chip including an imaging array electrically coupled to a conductive pad, and further including first and second utility apertures passing through the imaging chip;
(b) a lens optically coupled to the imaging array;
(c) an umbilical, including a conductive line carried by the second utility aperture, said conductive line being directly electrically coupled to the conductive pad; and
(d) a lens holder disposed in contact with a top surface of the solid state imaging chip and over the first utility aperture and leaving the second utility aperture uncovered.

12. The miniaturized imaging device of claim 11, wherein said lens holder comprises at least one aperture disposed through the lens holder and along a longitudinal axis of said lens holder.

13. The miniaturized imaging device of claim 12, wherein the at least one aperture of the lens holder is collinear with the first utility aperture disposed within the solid state imaging chip.

14. The miniaturized imaging device of claim 11, wherein the lens holder covers a substantial portion of the solid state imaging chip.

15. The miniaturized imaging device of claim 14, wherein the lens holder is oriented such that the second utility aperture of the solid state imaging chip is not covered by the lens holder.

16. The miniaturized imaging device of claim 11, wherein the lens holder comprises a plurality of parallel apertures disposed along a longitudinal axis of the lens holder.

17. The miniaturized imaging device of claim 16, wherein the solid state imaging chip comprises a plurality of utility apertures oriented substantially collinear with the plurality of parallel apertures of the lens holder.

* * * * *